(12) United States Patent
Arlt (10) Patent No.: US 10,485,413 B2
(45) Date of Patent: Nov. 26, 2019

(54) ENDOSCOPIC SURGICAL INSTRUMENT (71) Applicant: DANNORITZER Medizintechnik GmbH & Co. KG, Tuttlingen (DE)

(72) Inventor: Matthias Arlt, Neuhausen ob Eck (DE)

(73) Assignee: DANNORITZER Medizintechnik GmbH & Co. KG, Tuttlingen (DE)

( * ) Notice: Subject to any disclaimer, the term of this patent is extended or adjusted under 35 U.S.C. 154(b) by 0 days.

(21) Appl. No.: 16/062,145

(22) PCT Filed: Dec. 16, 2016

(86) PCT No.: PCT/EP2016/081592
§ 371 (c)(1),
(2) Date: Jun. 14, 2018

(87) PCT Pub. No.: WO2017/103217
PCT Pub. Date: Jun. 22, 2017

(65) Prior Publication Data
US 2018/0368672 A1 Dec. 27, 2018

(30) Foreign Application Priority Data

Dec. 18, 2015 (DE) .................... 20 2015 106 940 U (51) Int. Cl.
*A61B 1/04* (2006.01)
*A61B 1/12* (2006.01)
(Continued)

(52) U.S. Cl.
CPC ............ *A61B 1/126* (2013.01); *A61B 1/0014* (2013.01); *A61B 1/00094* (2013.01);
(Continued)

(58) Field of Classification Search
CPC ............ A61B 1/00066; A61B 1/00071; A61B 1/00103; A61B 1/00105; A61B 1/00147;
(Continued)

(56) References Cited

U.S. PATENT DOCUMENTS 5,088,998 A * 2/1992 Sakashita ............. A61B 18/149
600/105
5,287,845 A * 2/1994 Faul ................... A61B 1/00135
600/135
(Continued)

FOREIGN PATENT DOCUMENTS

DE 102013102024 A1 8/2014
EP 2095757 A1 9/2009
(Continued)

OTHER PUBLICATIONS

Search Report dated Jul. 1, 2016 issued in corresponding DE patent application No. 20 2015 106 940.5 (and partial English translation).
(Continued)

*Primary Examiner* — Matthew J Kasztejna
(74) *Attorney, Agent, or Firm* — Posz Law Group, PLC (57) ABSTRACT

An endoscopic surgical instrument includes at least one endoscopy shaft, with at least one suction and/or rinse unit, with at least one securing element, which is configured to secure the at least one endoscopy shaft on the at least one suction and/or rinse unit in a coupled state, and with at least one fixation unit, which is configured for a captive fixation of the at least one securing element on the at least one suction and/or rinse unit, wherein the at least one fixation unit comprises at least one cover element which, in a mounted state, encompasses the at least one securing element at least partly, wherein the at least one cover element comprises at least one operational recess for an operation of the at least one securing element.

8 Claims, 3 Drawing Sheets

(51) Int. Cl.
*A61B 1/00* (2006.01)
*A61B 17/34* (2006.01)

(52) U.S. Cl.
CPC ...... *A61B 1/00128* (2013.01); *A61B 17/3421* (2013.01); *A61B 2017/347* (2013.01); *A61B 2017/3454* (2013.01); *A61B 2218/001* (2013.01)

(58) Field of Classification Search
CPC .............. A61B 1/00154; A61B 1/0052; A61B 1/00119; A61B 1/00121; A61B 1/00128
USPC .................................. 600/105, 121–125, 136
See application file for complete search history.

(56) References Cited

U.S. PATENT DOCUMENTS

| | | | | |
|---|---|---|---|---|
| 5,290,294 A | * | 3/1994 | Cox | A61B 1/307 600/104 |
| 5,306,272 A | * | 4/1994 | Cohen | A61B 90/11 403/370 |
| 5,486,155 A | * | 1/1996 | Muller | A61B 1/00135 600/105 |
| 5,575,756 A | | 11/1996 | Karasawa et al. | |
| 5,843,040 A | * | 12/1998 | Exline | A61B 17/3462 604/164.11 |
| 6,086,530 A | * | 7/2000 | Mack | A61B 1/00135 600/121 |
| 6,196,967 B1 | * | 3/2001 | Lim | A61B 1/00128 600/125 |
| 6,282,442 B1 | * | 8/2001 | DeStefano | A61B 1/126 600/121 |
| 6,478,731 B2 | * | 11/2002 | Speier | A61B 1/00135 600/121 |
| 7,758,497 B2 | * | 7/2010 | Hem | A61B 1/00094 600/104 |
| 8,475,362 B2 | * | 7/2013 | Sohn | A61B 1/00006 600/105 |
| 9,345,386 B1 | * | 5/2016 | Cheng | A61B 1/00135 |

FOREIGN PATENT DOCUMENTS

JP 2009-201563 A 9/2009
WO 2015/179837 A1 11/2015

OTHER PUBLICATIONS

International Search Report of the International Searching Authority dated Mar. 29, 2017 issued in corresponding International Patent Application No. PCT/EP2016/081592.
International Preliminary Report on Patentability dated Nov. 20, 2017 issued in corresponding International Patent Application No. PCT/EP2016/081592 (English version attached).

* cited by examiner

ENDOSCOPIC SURGICAL INSTRUMENT

CROSS REFERENCE TO RELATED APPLICATIONS

This application is a U.S. national stage application of PCT/EP2016/081592 filed on Dec. 16, 2016, which claims priority to German Patent Application No. DE 20 2015 106 940.5 filed on Dec. 18, 2015, the contents of which are incorporated herein by reference.

STATE OF THE ART

The invention concerns an endoscopic surgical instrument with an endoscopy shaft and with a suction and/or rinse unit.

Furthermore, both JP 2009 201563 A and EP 2 095 757 A1 respectively disclose an endoscopic surgical instrument with an endoscopy shaft, with a suction and/or rinse unit, with a securing element, which is configured to secure the at least one endoscopy shaft on the at least one suction and/or rinse unit in a coupled state, and with a fixation unit, which is configured for a captive fixation of the at least one securing element on the at least one suction and/or rinse unit.

Moreover, an endoscopic surgical instrument with a removable eyepiece adaptor is already known from U.S. Pat. No. 5,575,756.

It has already been proposed that the endoscopic surgical instrument comprises a securing nut, which is configured for a securing of the endoscopy shaft on the suction and/or rinse unit.

The objective of the invention is in particular to make a generic endoscopic surgical instrument available which has improved characteristics regarding a fixation of the endoscopy shaft on the suction and/or rinse unit, wherein in particular a loss of the securing nut, in a disassembled state of the endoscopic surgical instrument, is to be prevented. The objective is achieved according to the invention by the features of patent claim 1 while advantageous implementations and further developments of the invention may be gathered from the subclaims.

Advantages of the Invention

The invention is based on an endoscopic surgical instrument with at least one endoscopy shaft, with at least one suction and/or rinse unit, with at least one securing element, which is configured to secure the at least one endoscopy shaft on the at least one suction and/or rinse unit in a coupled state, and with at least one fixation unit, which is configured for a captive fixation of the at least one securing element on the at least one suction and/or rinse unit.

It is proposed that the at least one fixation unit comprises at least one cover element which, in a mounted state, encompasses the at least one securing element at least partly, wherein the at least one cover element comprises at least one operational recess for an operation of the at least one securing element. This allows achieving, in a structurally simple and advantageously cost-competitive manner, a preferably reliable captive securing of the at least one securing element in a disassembled state of the endoscopic surgical instrument, in particular for cleaning.

A "suction and/or rinse unit" is in particular to mean, in this context, a unit at least for rinsing, in particular rinsing with a liquid, and/or for suctioning a liquid during a surgical intervention. The suction and/or rinse unit is preferentially implemented to be couplable with at least one hose, in particular a suction hose and/or a rinsing hose. The suction and/or rinse unit is preferably implemented to be couplable with at least one external pump via the at least one hose. "Configured" is in particular to mean specifically implemented, designed and/or equipped. By an object being configured for a certain function is in particular to be understood that the object fulfills and/or implements said certain function in at least one application state and/or operation state.

A "securing" is in particular to mean, in this context, that a movement of the at least one suction and/or rinse unit relative to the at least one endoscopy shaft is prevented in at least one direction. Preferably the at least one securing element is configured to secure the at least one suction and/or rinse unit, in particular against slipping, in a longitudinal direction of the at least one endoscopy shaft. In an assembled state the at least one securing element prevents a relative movement between the at least one suction and/or rinse unit and the at least one endoscopy shaft parallel to the longitudinal direction of the at least one endoscopy shaft at least approximately completely. The at least one securing element is preferably configured for a form-fit securing. It is however also conceivable that the at least one securing element is provided alternatively or additionally to a force-fit securing. The at least one securing element is particularly preferably configured for a releasable securing, in particular a manually and toollessly releasable securing, of the suction and/or rinse unit relative to the at least one endoscopy shaft.

It is further proposed that the at least one securing element is embodied as a securing nut. This allows achieving a preferably cost-effective, preferably compact and structurally simple implementation of the at least one securing element. However, other implementations of the at least one securing element, which are deemed expedient by someone skilled in the art, are also conceivable, like for example as a securing screw, as a clamp element, as a bayonet element and/or as a securing pin. The securing nut comprises an interior thread and an operational outer surface, which is implemented in such a way that it is operable, preferably operable without tools and manually, by an operator of the endoscopic surgical instrument. In a preferred exemplary embodiment the operational outer surface of the securing nut is embodied at least partially grooved. However, other implementations of the operational outer surface of the securing nut, which are deemed expedient by someone skilled in the art, are also conceivable, like for example as a hex socket.

As a result of the at least one fixation unit comprising at least one cover element which, in a mounted state, encompasses the at least one securing element at least partly, an advantageously simple and preferentially reliable captive securing of the at least one securing element is achievable. In an assembled state, the at least one cover element encompasses the at least one securing element at least partly in at least one plane, which plane is preferably arranged perpendicularly to a direction in which the at least one securing element secures the at least one suction and/or rinse unit relative to the at least one endoscopy shaft in an assembled state. Preferably the at least one cover element comprises at least two regions, which are arranged in particular spaced apart from one another and are, in an assembled state of the at least one fixation unit, arranged around the at least one securing element, preferably in an equally distributed fashion. The at least two regions of the at least one cover element are preferentially arranged over an angle range in particular of more than 180°, preferably of more than 270° and particularly preferably of at least approximately 360°. Preferably the at least two regions of the at least one cover element together cover an angle range in particular of at least 90°, preferentially of at least 120° and especially preferentially of at least 180° around the at least one securing element.

It is also proposed that the at least one cover element is fixedly connected to the at least one suction and/or rinse unit at least partly. In this way a preferably reliable implementation of the fixation unit is achievable. The at least one cover element is preferably connected to the at least one suction and/or rinse unit at least partially by substance-to-substance bond. The at least one cover element is particularly preferably at least partially welded with the at least one suction and/or rinse unit, in particular by laser welding. It is however also conceivable that the at least one cover element and the at least one suction and/or rinse unit are connected at least partially in another way that is deemed expedient by someone skilled in the art, e.g. by a force-fit connection or by a soldered or adhesive connection. "Fixedly connected" is in particular to mean, in this context, that the at least one cover element and at least a portion of the at least one suction and/or rinse unit are coupled captively and non-separably, in particular avoiding damage and/or destruction of at least one of the connected structural components.

Beyond this it is proposed that the at least one cover element is embodied at least partly of metal. This allows achieving an advantageously robust and moreover cost-competitive implementation of the at least one cover element. It is also conceivable that, alternatively or additionally, the at least one cover element is embodied at least partly of a different material that is deemed expedient by someone skilled in the art, e.g. of a synthetic material.

It is also proposed that the at least one cover element is embodied at least partially pot-shaped. In this way a structurally simple, advantageously compact implementation of the at least one cover element is achievable. By "pot-shaped" is in particular to be understood, in this context, that the at least one cover element comprises at least one region having a main extension surface that is implemented at least approximately planar, and comprises at least one region having a main extension surface that is implemented at least partly in a curved fashion, wherein surface normals of the main extension surfaces of the at least two regions extend perpendicularly to one another.

As a result of the at least one cover element comprising at least one operational recess for an operation of the at least one securing element, it is possible to achieve an advantageously operator-friendly and preferably comfortable operation and/or actuation of the at least one securing element. Moreover a preferentially light-weight implementation of the at least one cover element is achievable. The at least one operational recess is delimited at least partly by the at least one cover element. An "operational recess" is in particular to mean a region, in particular a material-free region, of the at least one cover element, which is configured to facilitate contacting of the at least one securing element by the operator of the endoscopic surgical instrument for the purpose of an operation and/or actuation of the at least one securing element. The at least one operational recess preferably features dimensions allowing an operation and/or actuation of the at least one securing element by means of a finger.

Moreover it is proposed that, in a mounted state of the at least one fixation unit, the at least one securing element is configured at least partly for a tool-free securing and/or release of the at least one endoscopy shaft with the at least one suction and/or rinse unit. In this way an advantageously simple, preferably operator-friendly operation and/or actuation of the at least one securing element is achievable.

It is furthermore proposed that the endoscopic surgical instrument comprises at least one locking unit, which is configured for a rotationally fixed locking at least of a portion of the suction and/or rinse unit relative to the at least one endoscopy shaft. This allows achieving an advantageously high level of operation comfort of the endoscopic surgical instrument, in particular during a surgical intervention. A "rotationally fixed locking" is in particular to mean, in this context, a coupling of the at least one suction and/or rinse unit with the at least one endoscopy shaft while avoiding a movement along at least one direction, in particular a rotational movement around an axis extending in parallel to the longitudinal direction of the at least one endoscopy shaft.

The endoscopic surgical instrument according to the invention is herein not to be restricted to the application and implementation described above. In particular, for the purpose of fulfilling a functionality that is described here, the endoscopic surgical instrument according to the invention may comprise a number of individual elements, structural components and units that differs from a number mentioned herein.

DRAWINGS

Further advantages will become apparent from the following description of the drawings. The drawings show an exemplary embodiment of the invention. The drawings, the description and the claims contain a plurality of features in combination. Someone skilled in the art will purposefully also consider the features separately and will find further expedient combinations.

It is shown in.

DESCRIPTION OF THE EXEMPLARY EMBODIMENT

Figure 1:
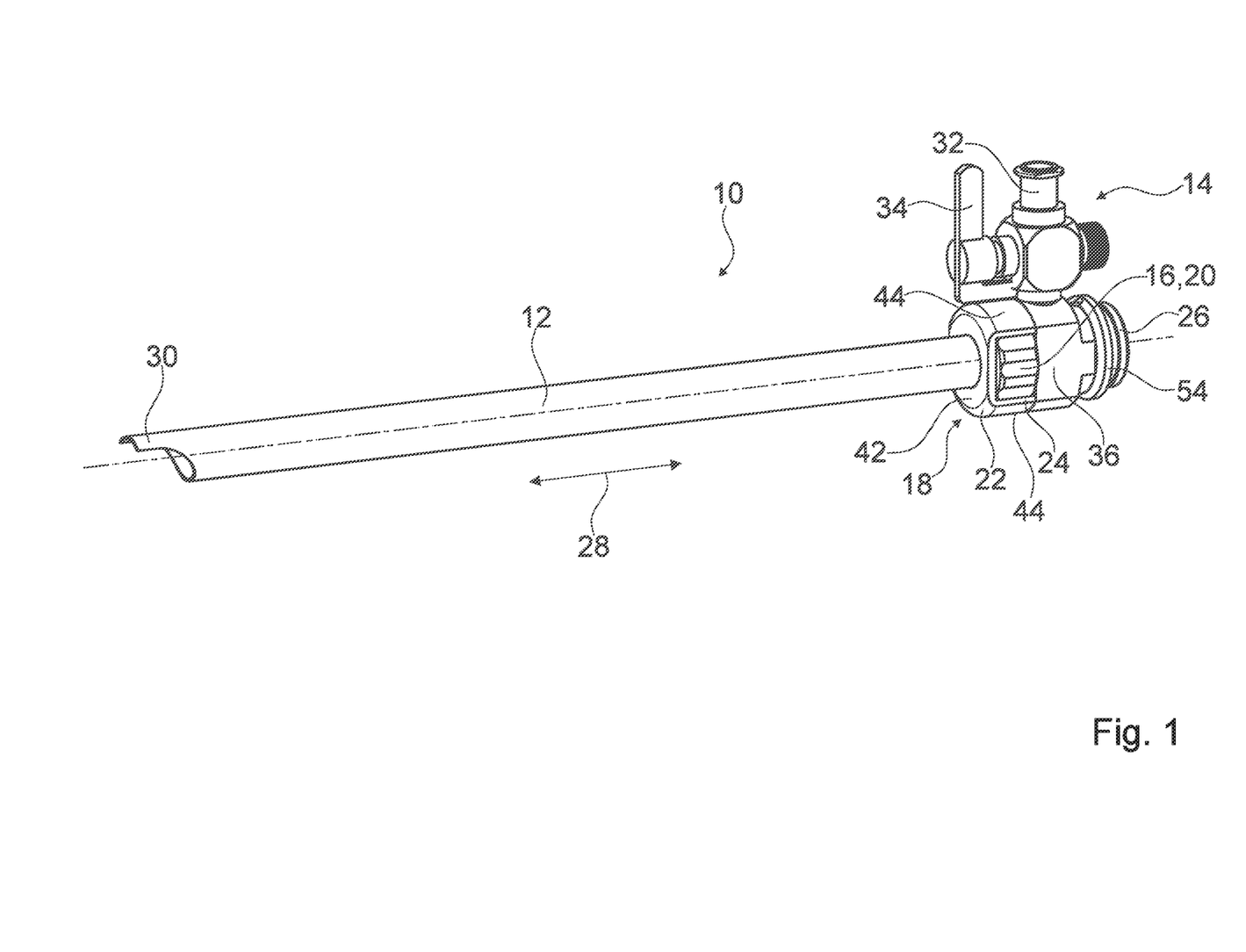
FIG. 1 an endoscopic surgical instrument in an assembled state in a perspective side view, FIG. 2 the endoscopic surgical instrument in a disassembled state in an exploded representation, FIG. 3 a portion of a suction and/or rinse unit of the endoscopic surgical instrument with a fixation unit, in an exploded representation, and FIG. 4 a flow chart of a method for assembly of the endoscopic surgical instrument.
Figure 2:
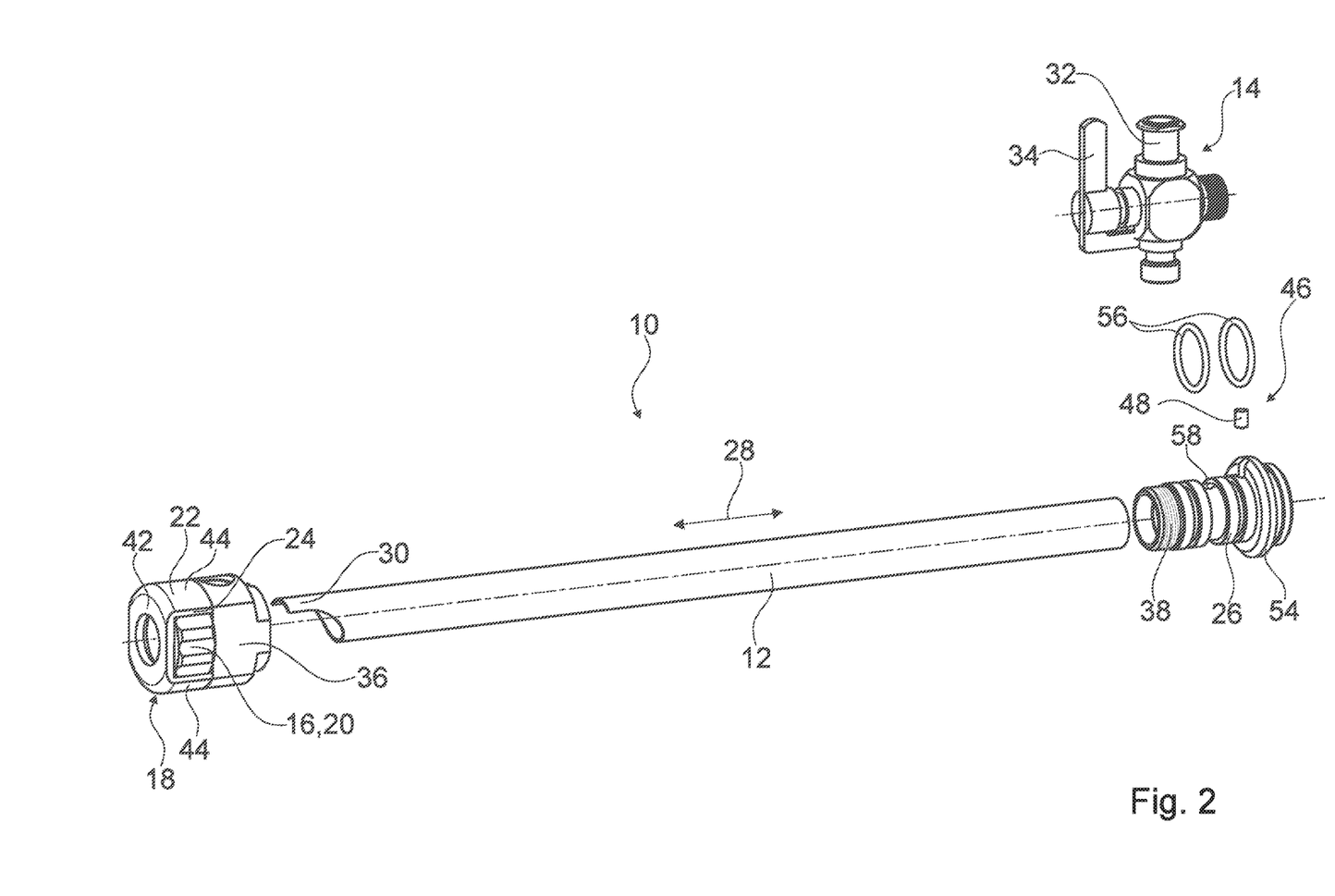

FIGS. 1 and 2 show an endoscopic surgical instrument 10 with at least one suction and/or rinse unit 14 and with at least one endoscopy shaft 12. The endoscopic surgical instrument 10 comprises a suction and/or rinse unit 14 and an endoscopy shaft 12. The endoscopy shaft 12 is embodied of metal. The endoscopy shaft 12 is implemented tube-shaped. The endoscopy shaft 12 has an outer diameter of 8 mm. The endoscopy shaft 12 has an inner diameter of 7.2 mm. The endoscopy shaft 12 has a length of 150 mm. The endoscopy shaft 12 is embodied as a rigid endoscopy shaft. The endoscopy shaft 12 comprises a beak-shaped tip 30. However, other implementations and/or dimensions of the endoscopy shaft 12, which are deemed expedient by someone skilled in the art, are also conceivable. The endoscopic surgical instrument 10 comprises at least one coupling element 26, which is connected to the endoscopy shaft 12 and is configured for a coupling of the endoscopy shaft 12 with the suction and/or rinse unit 14. The endoscopic surgical instrument 10 comprises precisely one coupling element 26. It is however also conceivable that the endoscopic surgical instrument 10 comprises more than one coupling element 26. Viewed in a longitudinal direction 28 of the endoscopy shaft 12, the coupling element 26 is arranged on an end of the endoscopy shaft 12 that faces away from the beak-shaped tip 30. The coupling element 26 is fixedly connected to the endoscopy shaft 12. The coupling element 26 is connected to the endoscopy shaft 12 by substance-to-substance bond. The coupling element 26 is connected to the endoscopy shaft 12 by a welded connection. The coupling element 26 is connected to the endoscopy shaft 12 by a laser-welded connection.

The suction and/or rinse unit 14 comprises at least one connection element 32 for a connection of a hose. The suction and/or rinse unit 14 comprises exactly one connection element 32, which is configured for a connection of a hose. It is however also conceivable that the suction and/or rinse unit 14 comprises more than one connection element 32, in particular two connection elements 32. The suction and/or rinse unit 14 further comprises at least one adjusting element 34, which is configured for an adjustment of a flow-through quantity through the suction and/or rinse unit 14 by an operator of the endoscopic surgical instrument 10. The adjusting element 34 is embodied as a mechanical adjusting element. The adjusting element 34 is implemented by a rotatably supported adjustment lever. The suction and/or rinse unit 14 comprises at least one accommodating element 36, which is configured for a coupling with the endoscopy shaft 12. The suction and/or rinse unit 14 comprises exactly one accommodating element 36. It is however also conceivable that the suction and/or rinse unit 14 comprises more than one accommodating element 36. The accommodating element 36 of the suction and/or rinse unit 14 is embodied correspondingly to the coupling element 26 that is connected to the endoscopy shaft 12. The accommodating element 36 is embodied as a female Luer fitting.

The accommodating element 36, the adjusting element 34 and the connection element 32 of the suction and/or rinse unit 14 are embodied of metal. The accommodating element 36, the adjusting element 34 and the connection element 32 of the suction and/or rinse unit 14 are made of stainless steel. The accommodating element 36, the adjusting element 34 and the connection element 32 of the suction and/or rinse unit 14 constitute an assembly unit. The accommodating element 36, the adjusting element 34 and the connection element 32 of the suction and/or rinse unit 14 are fixedly connected. The accommodating element 36 and the connection element 32 of the suction and/or rinse unit 14 are connected via substance-to-substance bond. It is however also conceivable that the accommodating element 36 and the connection element 32 of the suction and/or rinse unit 14 are connected at least partly via a form-fit and/or force-fit connection. The accommodating element 36 and the connection element 32 of the suction and/or rinse unit 14 are welded with one another. The accommodating element 36 and the connection element 32 of the suction and/or rinse unit 14 are connected via a laser-welded connection. It is however also conceivable that the accommodating element 36 and the connection element 32 of the suction and/or rinse unit 14 are connected in a different way that is deemed expedient by someone skilled in the art, like for example via an adhesive bond or a press-fitted connection. In an assembled state the accommodating element 36 engages around the coupling element 26 which is connected to the endoscopy shaft 12, at least partly. In an assembled state the accommodating element 36 completely engages around the coupling element 26 in a plane that is arranged perpendicularly to the longitudinal direction 28 of the endoscopy shaft 12.

The endoscopic surgical instrument 10 further comprises at least one securing element 16, which is configured to secure the at least one endoscopy shaft 12 on the at least one suction and/or rinse unit 14 in a coupled state. The endoscopic surgical instrument 10 comprises exactly one securing element 16 for a securing of the endoscopy shaft 12 relative to the suction and/or rinse unit 14. It is however also conceivable that the endoscopic surgical instrument 10 comprises more than one securing element 16. The securing element 16 is embodied as a securing nut 20. The securing element 16 is configured for a securing of the suction and/or rinse unit 14, relative to the endoscopy shaft 12, in a longitudinal direction 28 of the endoscopy shaft 12. The securing element 16 is made of metal. The securing element 16 is implemented in such a way that it is operable without tools. For the securing of the suction and/or rinse unit 14 relative to the endoscopy shaft 12, the securing element 16 is screwed onto a thread 38. The coupling element 26 which is connected to the endoscopy shaft 12, comprises the thread 38. The thread 38 is embodied as an exterior thread. The securing element 16 has an interior thread 40.

Figure 3:
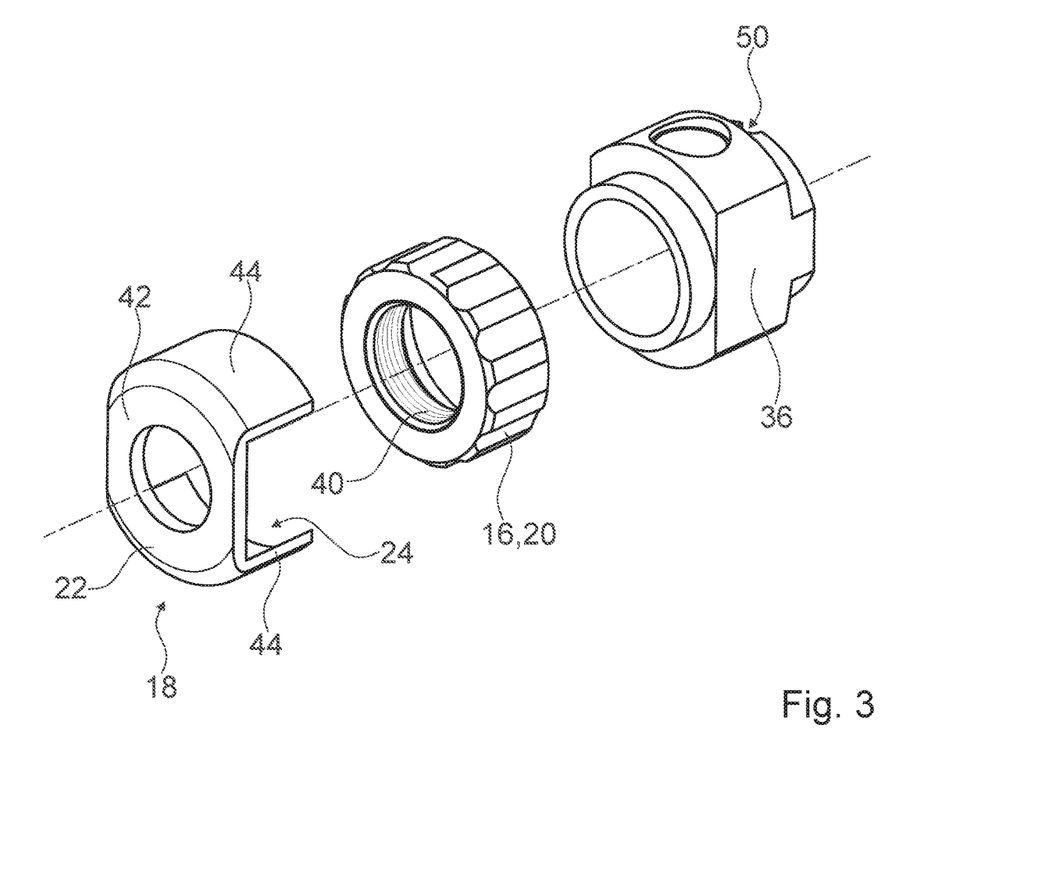

The endoscopic surgical instrument 10 also comprises at least one fixation unit 18, which is configured for a captive fixation of the securing element 16 on the suction and/or rinse unit 14. The endoscopic surgical instrument 10 comprises precisely one fixation unit 18. The fixation unit 18 comprises at least one cover element 22 which, in a mounted state, encompasses the securing element 16 at least partially. The fixation unit 18 comprises precisely one cover element 22. It is however also conceivable that the fixation unit 18 comprises more than one cover element 22. The cover element 22 partly encompasses the securing element 16 in at least one plane. The cover element 22 partly encompasses the securing element 16 in at least one plane, which is arranged perpendicularly to a rotary axis of the securing element 16. In an assembled state of the endoscopic surgical instrument 10, the rotary axis of the securing element 16 extends parallel to the longitudinal direction 28 of the endoscopy shaft 12. The cover element 22 is implemented at least partially of metal. The cover element 22 is completely implemented of metal. It is however also conceivable that the cover element 22 is made of a different material that is deemed expedient by someone skilled in the art, e.g. a synthetic material. The cover element 22 is, at least partially, fixedly connected to the suction and/or rinse unit 14. The cover element 22 is fixedly connected to the suction and/or rinse unit 14. The cover element 22 is connected to the suction and/or rinse unit 14 by substance-to-substance bond. The cover element 22 is connected to the suction and/or rinse unit 14 by laser welding. The cover element 22 is connected to the accommodating element 36 of the suction and/or rinse unit 14.

The cover element 22 is embodied at least partially pot-shaped. The cover element 22 comprises at least one operational recess 24 for operating the securing element 16. The cover element 22 comprises two operational recesses 24. However, a differing number of operational recesses 24 is also conceivable. The cover element 22 comprises a first region 42 and two further regions 44. The first region 42 has a circular-arc-shaped contour. The first region 42 is embodied plate-shaped. The two further regions 44 of the cover element 22 are arranged adjacently to the first region 42. The two further regions 44 of the cover element 22 are arranged directly adjacently to the first region 42. The first region 42 and the two further regions 44 of the cover element 22 are embodied in a one-part implementation. The two further regions 44 of the cover element 22 are embodied identically. The further regions 44 are each embodied plate-shaped and curved. The further regions 44 each comprise a longitudinal direction extending parallel to a surface normal of the first region 42 of the cover element 22. In an assembled state of the endoscopic surgical instrument 10, the surface normal of a main extension surface of the first region 42 of the cover element 22 extends parallel to the longitudinal direction 28 of the endoscopy shaft 28. The further regions 44 are respectively embodied curved around an axis that extends in parallel to the longitudinal direction of the further regions 44 and/or to the surface normal of the main extension surface of the first region 42. The further regions 44 are arranged on a circle line. The further regions 44 are arranged on a circular circumferential line of the first region 42. Viewed along a diameter of the first region 42, the further regions 44 are arranged opposite one another. In a circumferential direction of the cover element 22, the further regions 44 are arranged spaced apart. The further regions 44 delimit the operational recesses 24 in a circumferential direction. In a mounted state of the fixation unit 18, the securing element 16 is arranged between the further regions 44 of the cover element 22. The cover element 22 is connected to the suction and/or rinse unit 14 on respective ends of the further regions 44, each respective end facing away from the first region 42.

The cover element 22 has a greatest distance between the further regions 44 of 16.3 mm. Viewed perpendicularly to the distance between the further regions 44, the cover element 22 has a height of 8.3 mm. Viewed perpendicularly to the height of the cover element 22, the cover element 22 has a smallest width of 13 mm. The first region 42 of the cover element 22 has a thickness of 0.4 mm. Viewed in parallel to the surface normal of the main extension surface of the first region 42, the further regions 44 of the cover element 22 each have a height of 6.9 mm. A circle-shaped recess in the first region 42 of the cover element 22 has a diameter of 8.2 mm. Viewed in parallel to the main extension surface of the first region 42, the cover element 22 has a maximum extension of 17.5 mm. However, other dimensions deemed expedient by someone skilled in the art are also conceivable.

In a mounted state of the fixation unit 18, the securing element 16 is supported captively relative to the cover element 22 of the fixation unit 18 and relative to the accommodating element 36 of the suction and/or rinse unit 14. In a mounted state of the fixation unit 18, the securing element 16 is supported movably relative to the cover element 22 of the fixation unit 18 and relative to the accommodating element 36 of the suction and/or rinse unit 14. In a mounted state of the fixation unit 18, the securing element 16 is supported rotatably relative to the cover element 22 of the fixation unit 18 and relative to the accommodating element 36 of the suction and/or rinse unit 14. The fixation unit 18, the securing element 16 and the suction and/or rinse unit 14 constitute an assembly unit. The securing element 16 is in a mounted state of the fixation unit 18 configured at least partly for a tool-free securing and/or release of the endoscopy shaft 12 with the suction and/or rinse unit 14. The securing element 16 is, in a mounted state of the fixation unit 18, configured for a tool-free securing and/or release.

The endoscopic surgical instrument 10 furthermore comprises at least one locking unit 46, which is configured for a rotationally fixed locking of the suction and/or rinse unit 14 relative to the endoscopy shaft 12. The endoscopic surgical instrument 10 comprises precisely one locking unit 46. It is however also conceivable that the endoscopic surgical instrument 10 comprises more than one locking unit 46. The locking unit 46 is configured for a rotationally fixed locking of the accommodating element 36 of the suction and/or rinse unit 14 relative to the coupling element 26 that is fixedly connected to the endoscopy shaft 12. The locking unit 46 comprises at least one locking element 48. The locking unit 46 comprises precisely one locking element 48. It is however also conceivable that the locking unit 46 comprises more than one locking element 48. The locking element 48 is embodied cylinder-shaped. The locking element 48 is embodied pin-shaped. The locking element 48 has a diameter of 2 mm. The locking element 48 has a length of 2.7 mm. The locking element 48 is fixedly connected to the coupling element 26 which is coupled with the endoscopy shaft 12. The locking element 48 is connected to the coupling element 26 by substance-to-substance bond. The locking element 48 is welded with the coupling element 26. In an assembled state, a rotational symmetry axis of the locking element 48 is arranged perpendicularly to the longitudinal direction 28 of the endoscopy shaft 12. At least one locking recess 50, which is embodied correspondingly to the locking element 48, has been introduced in the accommodating element 36 of the suction and/or rinse unit 14. In the accommodating element 36 of the suction and/or rinse unit 14, two locking recesses 50, which are arranged offset in a circumferential direction, have been introduced. However, a different number of locking recesses 50, deemed expedient by someone skilled in the art, is also conceivable. Viewed in the circumferential direction of the accommodating element 36, the two locking recesses 50 are arranged offset by 90°.

Alternatively it is also conceivable that the endoscopic surgical instrument 10 comprises no locking unit 46 and the suction and/or rinse unit 14 is, in an assembled state, supported in such a way that it is rotatable relative to the endoscopy shaft 12.

Figure 4:
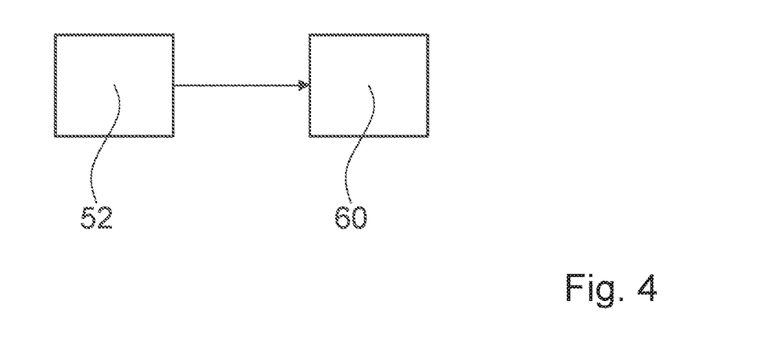

A method for an assembly of the endoscopic surgical instrument 10 comprises at least one method step 52, in which the suction and/or rinse unit 14 is positioned relative to the endoscopy shaft 12. In the method step 52 the accommodating element 36 of the suction and/or rinse unit 14 is slid onto the endoscopy shaft 12 in the longitudinal direction 28, from the tip 30 of the endoscopy shaft 12 towards the coupling element 26. The accommodating element 36 of the suction and/or rinse unit 14 herein engages around the endoscopy shaft 12. The suction and/or rinse unit 14 is shifted along the endoscopy shaft 12 in the longitudinal direction 28 until the accommodating element 36 of the suction and/or rinse unit 14 abuts on a stop 54 of the coupling element 26 which is arranged on an end of the coupling element 26 facing away from the endoscopy shaft 12. The stop 54 is embodied in a one-part implementation with the coupling element 26. Viewed from the tip 30 of the endoscopy shaft 12 towards the coupling element 26, the stop 54 delimits a movement of the suction and/or rinse unit 14 in a direction that is parallel to the longitudinal direction 28 of the endoscopy shaft 12.

Furthermore, in an assembled state at least one sealing element 56 which, in a state when the suction and/or rinse unit 14 is coupled with the accommodating element 36, implements a sealing. Two sealing elements 56 are coupled with the coupling element 26. It is however also conceivable that a different number of sealing elements 56 are provided. The sealing elements 56 are respectively implemented by a sealing ring. The sealing elements 56 are respectively implemented by an O-ring. At least one flow-through opening 58 has been introduced in the coupling element 26. Precisely one flow-through opening 58 has been introduced in the coupling element 26. It is however also conceivable that more than one flow-through opening 58 has been introduced in the coupling element 26. The flow-through opening 58 extends through an entire material thickness of the coupling element 26 and is configured to facilitate, in an operating state of the endoscopic surgical instrument 10, a liquid transport out of the endoscopy shaft 12 to the connection element 32 of the suction and/or rinse unit 14 and/or from the connection element 32 of the suction and/or rinse unit 14 into the endoscopy shaft 12. Viewed in the longitudinal direction 28 of the endoscopy shaft 12, the flow-through opening 58 is arranged between the two sealing elements 56.

The method comprises at least one further method step 60, in which the suction and/or rinse unit 14 is rotated around a longitudinal axis of the endoscopy shaft 12, which extends in parallel to the longitudinal direction 28, into a desired position by the operator of the endoscopic surgical instrument 10, and is secured in this position by means of the securing element 14. For this purpose the operator rotates the suction and/or rinse unit 14 until one of the locking recesses 50 in the accommodating element 36 gets aligned with the locking element 48. Then the securing element 16 is screwed onto the thread 38 of the coupling element 26. As a result of this and at the same time by the engagement of the locking element 48 with the locking recess 50 the suction and/or rinse unit 14 is secured in a circumferential direction, viewed in a direction that is parallel to the longitudinal direction 28 of the endoscopy shaft 12 from the coupling element 26 towards the tip 30 of the endoscopy shaft 12. For the purpose of changing a positioning of the suction and/or rinse unit 14 relative to the endoscopy shaft 12 in a circumferential direction, the securing element 16 is released, the suction and/or release unit 14 is rotated, relative to the endoscopy shaft 12, in the circumferential direction until the other one of the locking recesses 50 gets aligned with the locking element 48, and then the securing element 16 is once again screwed onto the thread 38 of the coupling element 26.

The invention claimed is:

1. An endoscopic surgical instrument, comprising:
at least one endoscopy shaft,
at least one suction and/or rinse unit,
at least one securing element, which is configured to secure the at least one endoscopy shaft on the at least one suction and/or rinse unit in a coupled state, and
at least one fixation unit, which is configured for a captive fixation of the at least one securing element on the at least one suction and/or rinse unit, wherein
the at least one fixation unit comprises at least one cover element which, in a mounted state, encompasses the at least one securing element at least partly,
the at least one cover element comprises at least one operational recess for an operation of the at least one securing element,
the at least one cover element is embodied at least partially pot-shaped,
the operational recess is embodied as a lateral opening in a side wall of the pot-shaped cover element,
the side wall is at least partly formed at least substantially parallel to a longitudinal axis of the endoscopy shaft,
in an assembled state, the at least one securing element prevents a relative movement between the at least one suction and/or rinse unit and the at least one endoscopy shaft parallel to a longitudinal direction of the at least one endoscopy shaft via a form-fit connection,
the at least one securing element is rotatable around a rotary axis, and
the rotary axis of the at least one securing element extends parallel to the longitudinal direction of the endoscopy shaft.

2. The endoscopic surgical instrument according to claim 1, wherein the at least one securing element is embodied as a securing nut.

3. The endoscopic surgical instrument according to claim 1, wherein the at least one cover element is fixedly connected to the at least one suction and/or rinse unit at least partly.

4. The endoscopic surgical instrument according to claim 1, wherein the at least one cover element is embodied at least partly of metal.

5. The endoscopic surgical instrument according to claim 1, wherein in a mounted state of the at least one fixation unit, the at least one securing element is configured at least partly for a tool-free securing and/or release of the at least one endoscopy shaft with the at least one suction and/or rinse unit.

6. The endoscopic surgical instrument according to claim 1, comprising at least one locking unit, which is configured for a rotationally fixed locking at least of a portion of the suction and/or rinse unit.

7. An endoscopic surgical instrument, comprising:
at least one endoscopy shaft,
at least one suction and/or rinse unit,
at least one securing element, which is configured to secure the at least one endoscopy shaft on the at least one suction and/or rinse unit in a coupled state, and
at least one fixation unit, which is configured for a captive fixation of the at least one securing element on the at least one suction and/or rinse unit, wherein
the at least one fixation unit comprises at least one cover element which, in a mounted state, encompasses the at least one securing element at least partly,
the at least one cover element comprises at least one operational recess for an operation of the at least one securing element,
the at least one cover element is embodied at least partially pot-shaped,
the operational recess is embodied as a lateral opening in a side wall of the pot-shaped cover element,
the side wall is at least partly formed at least substantially parallel to a longitudinal axis of the endoscopy shaft,
in an area of the operational recess of the cover element, the securing element has a radial extension perpendicular to a longitudinal axis of the endoscopy shaft that is bigger than a radial extension of the cover element perpendicular to the longitudinal axis of the endoscopy shaft,
in an assembled state, the at least one securing element prevents a relative movement between the at least one suction and/or rinse unit and the at least one endoscopy shaft parallel to a longitudinal direction of the at least one endoscopy shaft via a form-fit connection,
the at least one securing element is rotatable around a rotary axis, and
the rotary axis of the at least one securing element extends parallel to the longitudinal direction of the endoscopy shaft.

8. An endoscopic surgical instrument, comprising:
at least one endoscopy shaft,
at least one suction and/or rinse unit, at least one securing element, which is configured to secure the at least one endoscopy shaft on the at least one suction and/or rinse unit in a coupled state, and at least one fixation unit, which is configured for a captive fixation of the at least one securing element on the at least one suction and/or rinse unit, wherein the at least one fixation unit comprises at least one cover element which, in a mounted state, encompasses the at least one securing element at least partly, the at least one cover element comprises at least one operational recess for an operation of the at least one securing element, the suction and/or rinse unit comprises at least one accommodating element, which is configured for a coupling with the endoscopy shaft, and the securing element, in the mounted state, is arranged between the cover element and the accommodating element, in an assembled state, the at least one securing element prevents a relative movement between the at least one suction and/or rinse unit and the at least one endoscopy shaft parallel to a longitudinal direction of the at least one endoscopy shaft via a form-fit connection, the at least one suction and/or rinse unit comprises at least one connection element for a connection of a hose, and the at least one connection element and the accommodation element are fixedly connected.

* * * * *